United States Patent [19]

Driskell

[11] Patent Number: 4,738,623
[45] Date of Patent: Apr. 19, 1988

[54] DENTAL IMPLANT AND METHOD

[75] Inventor: Thomas D. Driskell, Westerville, Ohio

[73] Assignee: Quintron, Inc., Galena, Ohio

[21] Appl. No.: 896,978

[22] Filed: Aug. 15, 1986

[51] Int. Cl.⁴ .............................................. A61C 8/00
[52] U.S. Cl. .................................................... 433/173
[58] Field of Search ................ 433/173, 174, 175, 176

[56] References Cited
U.S. PATENT DOCUMENTS 4,177,562 12/1979 Miller ................................... 433/174
4,547,157 10/1985 Driskell ................................ 433/173
4,588,381 5/1986 Caracciolo .......................... 433/173

Primary Examiner—Robert Peshock
Attorney, Agent, or Firm—Frank H. Foster

[57] ABSTRACT

A dental implant having a root member formed with a narrowed shoulder at its top around which bone growth stimulating material is packed. The head member has an upstanding taper for receipt of a crown, a frusto-spherical basal portion extending down from the upstanding taper and a tapered rod or socket for connection to the root. The upstanding taper and the root connector rod or socket are aligned along radii of the sphere which defines the spherical surface of the basal portion.

26 Claims, 3 Drawing Sheets

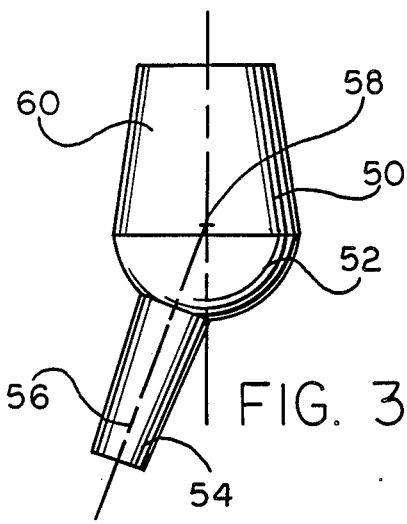
FIG. 3
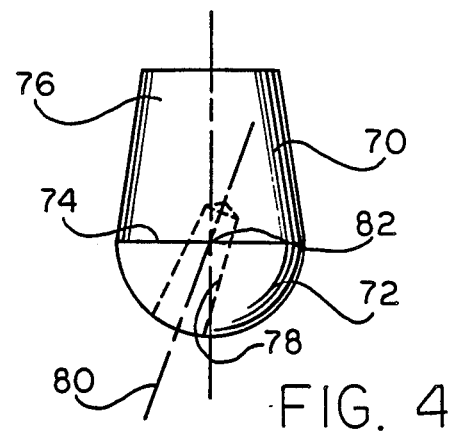
FIG. 4
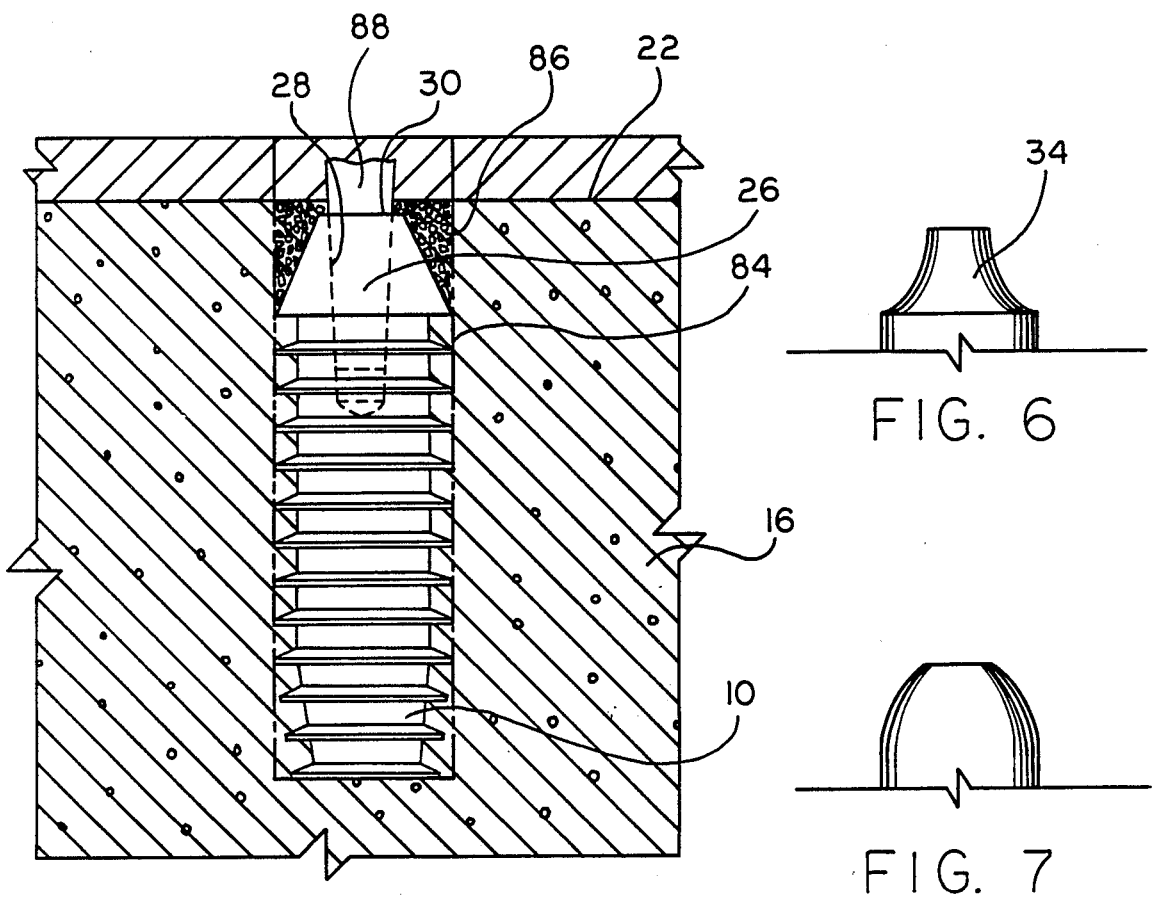
FIG. 5
FIG. 6
FIG. 7

DENTAL IMPLANT AND METHOD

TECHNICAL FIELD

This invention relates generally to dental implants for surgical implantation in the mouth of a patient for supporting a prosthetic crown or bridge in order to replace the tooth of the patient, and more particularly relates to such an implant having a head member which is formed in a manner which can be easily machined and more accurately fitted and having a separate root member which is formed and surgically positioned in a manner such that the formation of improved gingival and subgingival interfacing with the implant is promoted.

BACKGROUND ART

The natural teeth of a patient are often lost as a result of dental disease or trauma, making it desirable to replace a natural tooth with a prosthetic device. One type of prosthetic device is the dental endosteal or endosseous implant which is surgically positioned within the mandibular or maxillary alveolar bone of the patient and, after healing, is fitted with a tooth-simulating prosthesis or crown.

One type of dental implant, often called a submergible or two-stage, has a separate root member which is implanted by the oral surgeon in the alveolar bone of the patient. Following healing, a head member is mounted on the root and the crown is then mounted to the head member. This type of implant has met with a substantial degree of success.

Often the alveolar ridge is narrow and/or not aligned with the alignment of the nature teeth. To obtain parallelism with other implants or with the patient's natural teeth, it is necessary to provide implant heads that are on an oblique angle with respect to the root component or with straight heads so that the crown will be aligned with the natural teeth. Fabrication of angled heads is very difficult and the contours at the junction between the head member and the root member are generally awkward and not well adapted for good periodontal management of the gingival tissue at the head interface. It has been necessary to blend the junction of two truncated conical shapes of unlike angles, the axes of which intersect at an angle or don't intersect. This can not be done on a lathe without requiring a fair amount of subsequent hand filing or grinding to blend the junction.

Another way of fabricating these conventional angled heads is to mill them on a computer controlled milling machine. This process requires a rather complicated program as either the upper or lower conical shape can no longer be round in cross section but must elliptical if hand blending is to be avoided. Surface finish is also a problem and machining "chatter" is difficult to avoid.

This junction also becomes the "finish line" for the crown or bridge that subsequently will have to be mounted on this often rather crudely shaped head. This causes the subgingival contours of the head to be imprecise with undesirable overhangs and it becomes more difficult to obtain an acceptable mating of the crown or bridge without gaps and additional overhangs which will contribute to periodontal problems.

It is an object and purpose of the present invention to provide a head member structure which will allow the head member to be easily and relatively inexpensively machined and yet will make an optimum interfacing fit with the tissue.

Additionally, with previously known implants, two problems have been commonly encountered during healing. Conventionally, root members are used which have a connector member portion, such as a tapered post, or large diameter neck which extends up through the gingiva for later attachment to the head member. However, such protruding posts or necks cause problems for the dentist and the patient. The root member should not, if possible, be subjected to loading or forces incident upon it during mastication because such forces will move the implant and thus prevent a tight interlocking healing of the bone against the implant. Such a protruding connecting member also provides a site for infection or other disease problems during the healing process. Most existing "submergible" implants are barely so and often protrude through the tissue or become exposed.

It is an object and feature of the present invention that a root member be provided which is entirely submerged within the bone and does not protrude through the gingiva during healing.

Another difficulty experienced with the use of endosseous implants is the permanent loss of bone at the crest of the alveolar ridge around the root member. The bone may sometimes initially form and then die back to form, a crater or ditch in the bone about the region of the implant.

It is an object and feature of the present invention to provide a root member structure and a method for surgically implanting the root member which promotes the healing of the bone along the extension of the natural contour of the crest of the boney ridge and thus eliminate such a crater and regenerate the natural crestal contour.

BRIEF DISCLOSURE OF INVENTION

A root member formed in accordance with the present invention utilizes multiple, outwardly extending fins formed on the lower portion of the root member, such as annular fins or helical fins forming a screw thread, a narrowed upwardly and inwardly contoured shoulder formed above the fins and a head receiving female socket member formed through the top of the shoulder. Upon surgical insertion, synthetic, bone-growth-stimulating, grafting material or a combination including autogenous graft is packed in the void surrounding this narrowed shoulder. By positioning the female connector member on the root member, a small plug may be inserted in the female connecting member while the gingiva is permitted to heal over the entire implant.

The head member embodying the present invention is formed with an upstanding, generally tapered portion having a conical exterior surface for mounting the prosthetic crown and a basal portion having a convex, frusto-spherical exterior surface which extends downwardly from the tapered portion. The center of the sphere which defines the frusto-spherical surface lies on the axis of the conical surface so that the frusto-spherical and conical surfaces intersect along a circle. When surgically implanted, the spherical surface extends through the gingiva and alveolar crest toward the root member and provides an interface between the tissue and the head member which has a circular cross section, regardless of alignment of the head member. A connector member, such as the male portion of a locking taper, is formed on the basal portion of the head member along a radius of the sphere. This permits the head member to be easily machined and results in consistent root and head alignment and tissue interface. The particular angle that the connector makes with the axis of the conical surface determines the oblique angle between the root member and the head member. Thus, a family of head members may easily be manufactured to provide the dentist with a choice of angles he can make to accomplish proper alignment of the natural teeth within the alveolar bone.

BRIEF DESCRIPTION OF DRAWINGS

FIG. 3 is a view in side elevation of an alternative root member embodying the present invention.

FIG. 4 is a view in side elevation of yet another alternative head member embodying the present invention.

FIG. 5 is a view in vertical section of a root member embodying the present invention implanted in a patient's mouth during the healing process.

FIG. 6 is a view in side elevation of a portion of an alternative embodiment of a root member of the present invention showing an alternative shoulder construction.

FIG. 7 is a view in side elevation illustrating yet another alternative shoulder construction.

Figure 1:
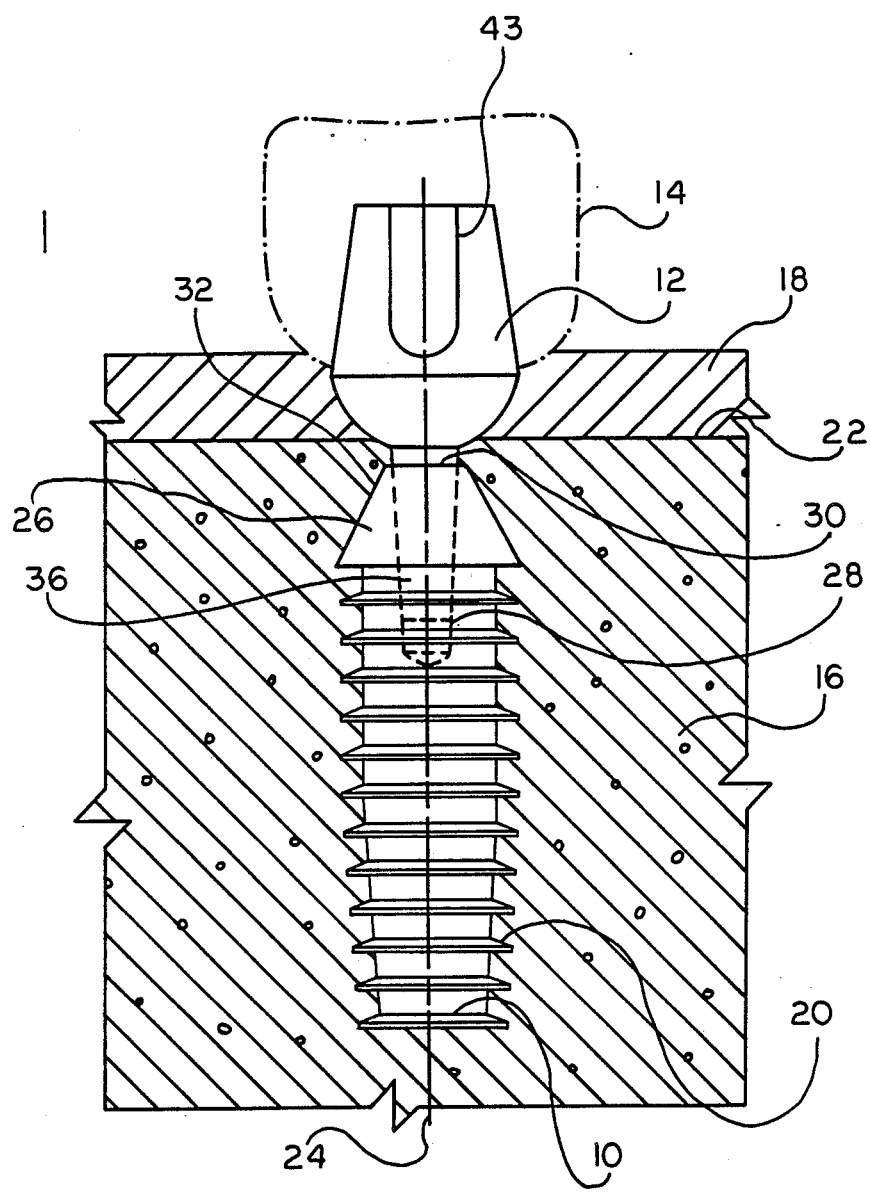
FIG. 1 is a view in vertical section of a dental implant embodying the present invention and implanted within a patient's mouth.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

FIG. 1 illustrates an entire implant unit embodying the present invention. It has a root member 10 upon which a head member 12 is mounted. A crown 14 is, in turn, mounted upon the head member 12. The root is implanted in the alveolar bone 16 and, of course, covered by gingiva 18.

The root member 10 has a plurality of outwardly extending fins 20 formed on a lower portion of the root member 10. In the description of the invention, the terms upper and lower are used with respect to depth within the bone and not with respect to the center of the earth. Thus, "lower" refers to a portion of the implant which is implanted deeper within the bone and "upper" refers to a portion more proximal to the crest 22 of the bone or to the gingiva 18. These fins 20 are formed substantially perpendicularly to the central axis 24 of the root member 10 in the manner which is known and illustrated, for example, in U.S. Pat. No. 3,950,850.

A narrowed, upperwardly extending tapered shoulder 26 extends smoothly and continuously above the fins, but when the root member 10 is implanted the shoulder is positioned below the crest 22 of the bone 16.

An upwardly opening, head-receiving, female socket 28 is formed into the root member through the top 30 of the shoulder 26. As illustrated, the preferred shoulder 26 is tapered to a very narrow upper rim 32. The surface of the tapered shoulder 26 is preferably substantially at an angle with the axis 24 of between 5 and 60 degrees, most preferably within 10 to 45 degrees.

However, alternative, upwardly and inwardly smoothly contoured shoulders may also be used. For example, FIG. 6 illustrates an alternative shoulder configuration 34. Alternatively, the shoulder can be upwardly and outwardly contoured or convex as illustrated in FIG. 7.

Figure 2:
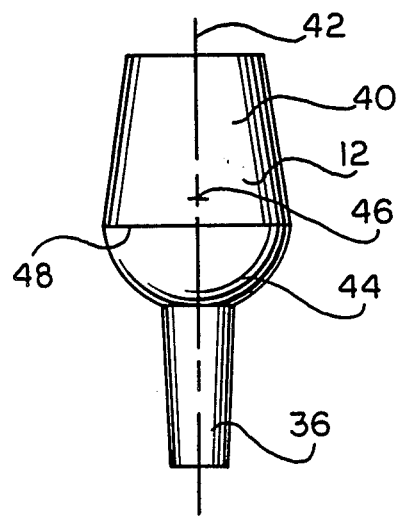
FIG. 2 is a view in side elevation of the head member of the embodiment illustrated in FIG. 1.

The preferred female socket member 28 formed into the top 30 of the shoulder 26 is a conventional female locking taper socket. The head member 12 is provided with a mating tapered post or rod 36. The head member 12 and its mating tapered rod 36 are illustrated in FIG. 2. The preferred head member 12 has an upstanding, generally tapered portion 40 having a conical, and preferably frusto-conical as illustrated, exterior surface with one or more anti-rotational flats 43 onto which a prosthetic crown 14, as illustrated in FIG. 1, is mounted. The conically tapered surface 40 has a central axis 42.

The head member 12 further includes a basal portion 44 having a convex frusto-spherical exterior surface which extends downwardly from the tapered frusto-conical surface 40. The center 46 of the sphere which defines the frusto-spherical surface lies on the axis 42 of the conical surface. This necessarily results in the intersection of the frusto-spherical surface 44 and the frusto conical surface 40 along a circle 48.

FIGS. 3 and 4 illustrate alternative head members embodying the present invention. In FIG. 3 the head member 50 has a frusto-spherical basal portion 52 and a tapered rod 54 which lies along a radius 56 of the center 58 of the sphere which defines the spheral surface of the basal portion 52. This connector rod 54 is at an oblique angle with the axis of the conical surface 60 of the head member 50 to accomodate the natural oblique angle which the alveolar ridge in some areas makes with the teeth alignment in the jaw.

Head members embodying the principles of the present invention may also be utilized with other root members. FIG. 4 illustrates a head member 70 having a frusto-spherical basal portion 72 which intersects along a circle 74 with the conical surface 76 of the head member 77. However, a female connector member is used, instead of a male, in the form of a tapered socket 78 formed in the head member 70. As with the tapered rod 54 of the embodiment illustrated in FIG. 3, the female socket 78 is aligned along a radius 80 from the center 82 of the sphere which defines the spherical surface 72.

The spherical surface defining the basal portion of the head member of the invention may be a hemisphere or less than a hemisphere. A cemented or threaded connection could also be used instead of a locking taper.

Referring to FIG. 5, the dentist surgically implants the root member by forming a root-receiving cavity 84 within the alveolar bone 16. This cavity may be drilled and reamed using conventional or specially designed surgical instruments and techniques. The root member 10 is inserted within the cavity 84 with the top 30 of the shoulder 26 one or two millimeters below the crest 22 of the bone 16. A plastic or metal plug 88 is inserted in the female socket 28 and trimmed to the proper height. Particles 86 of a natural or synthetic bone growth stimulating grafting material are then packed within the bone, below the crest and around the shoulder 26. These particles can be a mixture of autogenous graft material collected in the flutes of the reamers during cavity preparation or, more desirably, can be particles of a commercially available hydroxyapatite or a combination of the two and then the wound is closed. The particles 86 promote the ingrowth of tissue and blood supply and the eventual formation of bone in the void around the shoulder.

Following healing, the dentist surgically opens access to and removes the plug 88 and replaces it with the head member 12 as illustrated in FIG. 1. The head member 12 is positioned so that the frusto-spherical surface extends below the surface of the gingiva 18 and preferably down in through the crest 22 of the bone 16.

In the present invention, the formation of the narrowed shoulder on the root member provides a void in which the bone growth stimulating material can be packed to promote bone growth. The formation of the frusto-spherical basal portion on the head member provides an ideal tissue to prosthesis contour because it is circular and has no regions, such as corners, or undercuts causing increased tissue stress or repositories for bacteria or food particles. By forming the locking taper connector members of the head member along radii of the spherical surface, the head member is easily machined and is always properly blended and aligned.

Figure 9:
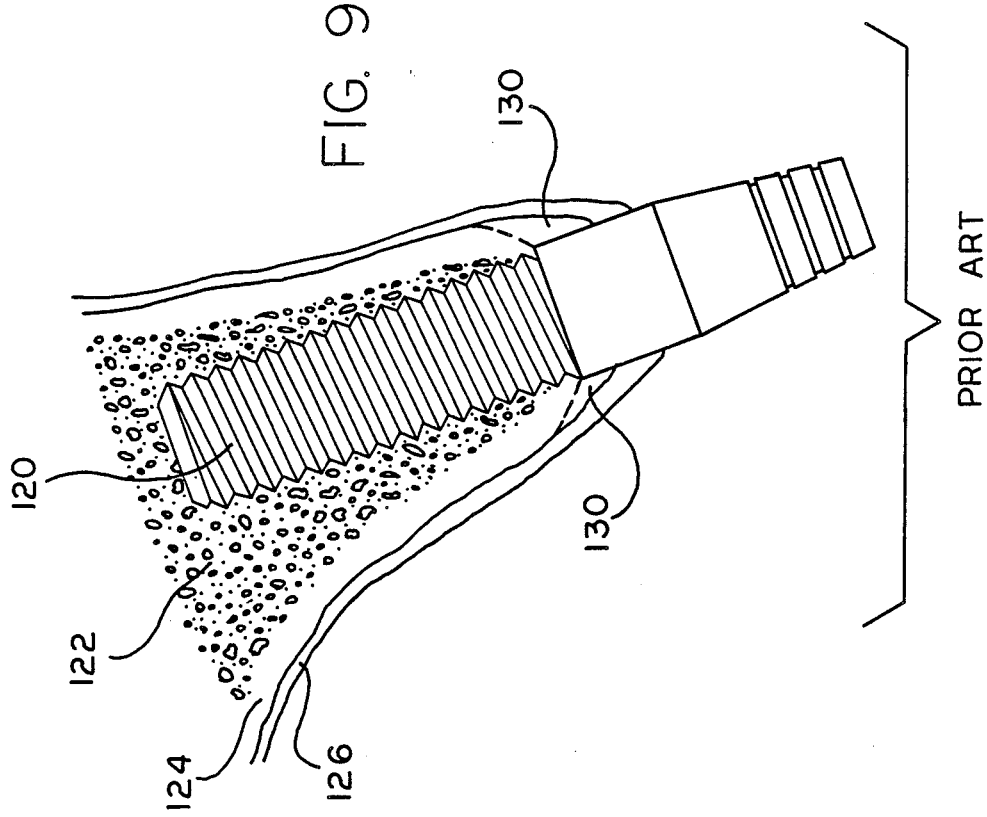
FIG. 9 is a similar view in vertical section of a prior art implant after initial healing.
Figure 8:
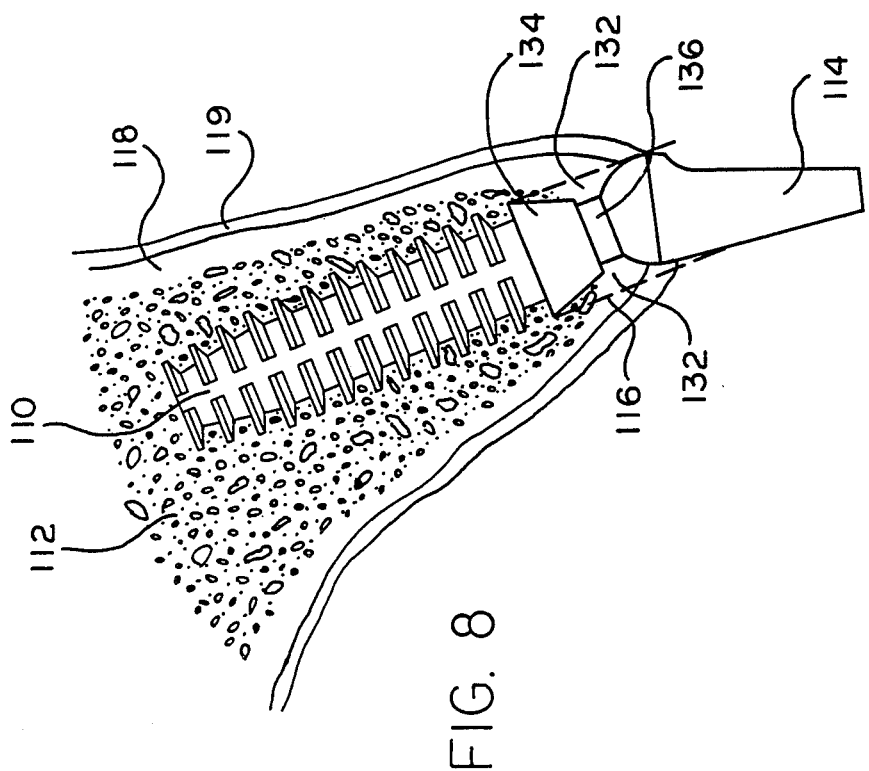
FIG. 8 is a view in vertical section of an implant embodying the present invention after healing.

Part of the effectiveness of Applicant's invention is illustrated in FIGS. 8 and 9. FIG. 8 shows a root member 110 embodying the present invention embedded in the bone 112 of a patient and carrying a head member 114. It illustrates the implant and surrounding tissue after healing has occurred. A portion of the original bore 116, which was prepared for insertion of the root member 110, is shown as dashed lines. The soft bone 112 is covered by the hard bone outer layer 118 and a soft tissue gingiva layer 119.

FIG. 9 shows a prior art implant 120 similarly positioned in bone 122. The soft bone 122 is covered by the hard bone outer layer 124 and the gingiva layer 126.

It is highly desirable with an implant that the cross section of the bone at the top of the ridge be maximized and be returned as nearly as possible to its original contour. However, with conventional implants a narrow wedge region 130 is formed on opposite sides of the implant. This region dies back after initial healing because its morphology makes it very difficult for the nearby tissue to vascularize and therefore supply blood to the bone in this region.

However, with Applicant's implant the region 132 surrounding the shoulder 134 of the root member 110 and surrounding the neck 136 of the head member 114 is a region into which the bone growth promoting materials may be packed to promote the growth of bone around the upper portion of the implant. The region has a morphology which does not deter vascularization.

While certain preferred embodiments of the present invention have been disclosed in detail, it is to be understood that various modifications may be adopted without departing from the spirit of the invention or scope of the following claims.

I claim:

1. An improved, submergible dental implant of the type having an endosseous root member for implantation in the maxillary or mandibular alveolar bone of a patient for supporting a prosthetic crown, wherein the improvement comprises:
    a narrowed, upwardly, inwardly and three dimensionally contoured shoulder formed surrounding the crestal end of the root member for implantation below the crest of the bone.

2. An implant in accordance with claim 1 wherein said shoulder is a smoothly continuous taper within a range of substantially 5 degrees to 60 degrees with the axis of the root member.

3. An implant in accordance with claim 1 or 2 wherein the shoulder is formed at the end of the root member and a female socket for receipt of a head member is formed into the root member through the top of the shoulder.

4. An implant in accordance with claim 1 wherein the shoulder is tapered with a relatively narrow upper rim.

5. An implant in accordance with claim 4 wherein said taper is at an angle substantially within the range of 5 degrees to 60 degrees with the axis of the root member.

6. An implant in accordance with claim 5 wherein said angle is substantially within the range of 10 degrees to 45 degrees.

7. In a dental implant, an improved head portion comprising:
    (a) a basal portion having a frusto-spherical exterior surface, the spherical surface having a center;
    (b) an upstanding generally tapered portion having a central axis aligned along a radial from the center of the spherical surface; and
    (c) a member aligned along a different radial of the spherical surface.

8. A dental implant in accordance with claim 5 and further having an endosseous root member for implantation in the maxillary or mandibular alveolar bone of a patient, and further comprising:
    a narrowed, upwardly, and three dimensionally contoured shoulder formed surrounding the crestal end of the root member for implantation below the crest of the bone.

9. An implant in accordance with claim 7 wherein said member of the head is a tapered rod extending downwardly from the frusto-spherical surface.

10. An implant in accordance with claim 7 wherein said member of the head is a tapered socket extending upwardly into said basal portion.

11. An implant in accordance with claim 9 or 10 whereiin the upstanding, conically tapered surface is truncated.

12. An implant in accordance with claim 8 wherein the shoulder is essentially tapered.

13. An implant in accordance with claim 12 wherein said taper is at an angle substantially within the range of 5 degrees to 60 degrees with the axis of the root member.

14. An implant in accordance with claim 13 wherein said angle is substantially within the range of 10 degrees to 45 degrees.

15. An implant in accordance with claim 8 wherein a female locking taper socket is formed into the top of the root member and the head member has a mating tapered rod.

16. An implant in accordance with claim 12 wherein a female locking taper socket is formed into the top of the root member and the head member has a mating tapered rod.

17. An implant in accordance with claim 13 wherein a female locking taper socket is formed into the top of the root member and the head member has a mating tapered rod.

18. An implant in accordance with claim 14 wherein a female locking taper socket is formed into the top of the root member and the head member has a mating tapered rod.

19. A method for implanting an endosseous dental implant root member in the maxillary or mandibular alveolar bone of a patient for supporting a prosthetic device, the method comprising:
 (a) forming a narrowed, upward, inwardly, and three-dimensionally contoured shoulder around the crestal end of the root member;
 (b) forming a root member receiving cavity in the bone;
 (c) positioning the root member in the cavity with said shoulder below the crest of the bone to provide a void around the shoulder extending between the shoulder and the natural extension of the crest of the bone, for the ingrowth of bone which is stressed by radial forces applied to the root member.

20. A method in accordance with claim 19 wherein said method further comprises packing the void around the shoulder and within the ridge with particles of a natural or synthetic bone grafting material.

21. A method in accordance with claim 19 wherein said shoulder is formed as a tapered shoulder.

22. A method in accordance with claim 19 or 21 wherein a socket is formed into the crestal end of the root member and a plug is inserted in said socket upon surgical implantation, left there during a period of initial healing and is then removed for mounting of a prosthesis to said socket.

23. A method in accordance with claim 22 wherein said void is packed with hydroxyapatite particles.

24. A method in accordance with claim 19, 20 or 21 wherein said void is packed with hydroxyapatite particles.

25. A method in accordance with claim 19 or 21 for additionally improving the interfacing contact between the gingiva covering said ridge and a prosthetic crown supporting head member mounted to the root member, the method comprising:
 (a) forming the head member with an upstanding generally tapered portion having a conical exterior surface for mounting a prosthetic crown, the conically tapered surface having a central axis, the head member further including a basal portion having a convex, frusto-spherical exterior surface extending downwardly from the tapered portion, the center of the sphere which defines the frusto-spherical surface lying on the axis of the conical surface whereby the frusto-spherical and conical surfaces intersect along a circle, and the head member further including a tapered rod extending downwardly from the spherical surface along a radius of said sphere for mating engagement with the female, head-receiving socket of said root member; and
 (b) mounting the head member on the root member with the frusto-spherical surface extending below the gingival surface whereby the gingiva forms a circular interface around the frusto-spherical surface.

26. A method in accordance with claim 25 wherein the head member is mounted with the frusto-spherical surface extending below the crest of said ridge.

* * * * *